US010951869B1

(12) United States Patent
Morales

(10) Patent No.: US 10,951,869 B1
(45) Date of Patent: Mar. 16, 2021

(54) SYSTEM FOR OPTIMIZING BLENDED VIDEO STREAMS

(71) Applicant: KARL STORZ Imaging, Inc., Goleta, CA (US)

(72) Inventor: Efrain Morales, Santa Ynez, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 0 days.

(21) Appl. No.: 16/711,218

(22) Filed: Dec. 11, 2019

(51) Int. Cl.
 H04N 9/64 (2006.01)
 H04N 9/68 (2006.01)
 H04N 9/77 (2006.01)
 H04N 5/225 (2006.01)
 H04N 5/265 (2006.01)
 A61B 1/04 (2006.01)
 A61B 1/00 (2006.01)

(52) U.S. Cl.
 CPC .......... H04N 9/646 (2013.01); A61B 1/0002 (2013.01); A61B 1/00045 (2013.01); A61B 1/043 (2013.01); H04N 5/2256 (2013.01); H04N 5/265 (2013.01); H04N 9/68 (2013.01); H04N 9/77 (2013.01); H04N 2005/2255 (2013.01)

(58) Field of Classification Search
 CPC ............ H04N 9/646; H04N 9/68; H04N 9/77; H04N 5/2256; H04N 5/265; H04N 2005/2255; A61B 1/0002; A61B 1/00045; A61B 1/043; G06T 2207/20212; G06T 2207/20221
 See application file for complete search history.

(56) References Cited

U.S. PATENT DOCUMENTS

| | | | | |
|---|---|---|---|---|
| 6,961,080 B2 * | 11/2005 | Richardson | ............... | G01J 3/10 348/79 |
| 8,531,512 B2 * | 9/2013 | Gono | ................... | A61B 1/0638 348/131 |
| 9,412,155 B2 * | 8/2016 | Steiner | ..................... | G06T 5/007 |
| 9,788,710 B2 * | 10/2017 | Kuramoto | ............ | A61B 1/0638 |
| 10,366,496 B2 * | 7/2019 | Bergstrom | ............... | H04N 5/04 |
| 10,523,856 B2 * | 12/2019 | Shukla | .................... | H04N 5/217 |
| 10,602,917 B2 * | 3/2020 | King | .................... | A61B 1/0005 |
| 2004/0114219 A1 * | 6/2004 | Richardson | ........ | G01N 21/6458 359/368 |
| 2007/0102623 A1 * | 5/2007 | Fengler | ............. | A61B 1/00186 250/208.1 |

(Continued)

*Primary Examiner* — Brian P Yenke
(74) *Attorney, Agent, or Firm* — Michael Loi

(57) ABSTRACT

An enhanced fluorescence imaging system includes a light source for emitting non-visible and visible light and an image sensor for capturing non-visible and visible light image data. Data processing hardware performs operations that include determining a non-visible value associated with an amount of non-visible light captured by the image sensor and applying a color map to each non-visible value to generate non-visible light selected color values. The operations also include weighting a visible light chroma value with a non-visible chroma value to generate weighted chroma values and combining luma values of each pixel of the visible light image data to the weighted chroma values. The operations also include generating RGB values based on the luma values of the visible light image data and the weighted chroma values and transmitting the RGB values to the display.

16 Claims, 11 Drawing Sheets

(56) References Cited

U.S. PATENT DOCUMENTS

| | | | |
|---|---|---|---|
| 2008/0088711 A1* | 4/2008 | Border | G06T 7/194 348/222.1 |
| 2010/0309315 A1* | 12/2010 | Hogasten | H04N 5/332 348/164 |
| 2015/0269742 A1* | 9/2015 | Bergstrom | H04N 5/23229 348/164 |
| 2016/0093034 A1* | 3/2016 | Beck | G06T 3/4061 345/617 |
| 2017/0061663 A1* | 3/2017 | Johnson | G06T 5/50 |
| 2017/0127926 A1* | 5/2017 | Kuramoto | A61B 1/00045 |
| 2017/0230558 A1* | 8/2017 | Morales | H04N 5/2351 |
| 2019/0239749 A1* | 8/2019 | Ishikawa | A61B 5/0071 |
| 2020/0126227 A1* | 4/2020 | Adiri | G06K 9/4652 |
| 2020/0143545 A1* | 5/2020 | Weng | G06T 5/50 |

\* cited by examiner

Red Chan  Blue Chan  Green Chan

| NON-VISIBLE LIGHT VALUE 210 | | COLOR MAPPED (GREEN) RGB VALUES 310R, 310G, 310B | |
|---|---|---|---|
| NVL | 50 | R | 0 |
| | | G | 50 |
| | | B | 0 |
| NVL | 150 | R | 0 |
| | | G | 150 |
| | | B | 0 |
| NVL | 250 | R | 0 |
| | | G | 250 |
| | | B | 0 |

First Replace Threshold 522 = 100
Second Replace Threshold 524 = 200

|   | 410 | 412 | 520 |
|---|-----|-----|-----|
| Y | 158 | 41  | 158 |
| Cb| 121 | 113 | 121 |
| Cr| 150 | 110 | 150 |

NVL = 50, 560a

|   | 410 | 412 | 520 |
|---|-----|-----|-----|
| Y | 158 | 92  | 158 |
| Cb| 121 | 84  | 103 |
| Cr| 150 | 73  | 112 |

NVL = 150, 560b

|   | 410 | 412 | 520 |
|---|-----|-----|-----|
| Y | 158 | 142 | 158 |
| Cb| 121 | 55  | 55  |
| Cr| 150 | 36  | 36  |

NVL = 250, 560c

FIG. 5

Maximum Value = 255

NVL = 50
|   | 134 | 620 |
|---|-----|-----|
| R | 200 | 200 |
| G | 150 | 200 |
| B | 150 | 150 |

← 860a

NVL = 150
|   | 134 | 620 |
|---|-----|-----|
| R | 200 | 200 |
| G | 150 | 255 |
| B | 150 | 150 |

← 860b

NVL = 250
|   | 134 | 620 |
|---|-----|-----|
| R | 200 | 200 |
| G | 150 | 255 |
| B | 150 | 150 |

SYSTEM FOR OPTIMIZING BLENDED VIDEO STREAMS

TECHNICAL FIELD

The disclosure relates to a fluorescence imaging system for medical procedures.

BACKGROUND

Endoscopes are commonly used to provide access to body cavities while decreasing the invasiveness of a surgical procedure. A fluorescence imaging system can include an endoscope, one or more light sources that emit both visible (e.g., white) light and non-visible (e.g., infrared) light, a camera control unit, and a display control unit. The visible light is typically used as a reference light or illuminating light, while the non-visible light is typically used as an excitation light. That is, the non-visible light is used to irradiate a fluorescent substance (e.g., dye) administered to a patient, which in turn causes the fluorescent substance to emit fluorescence light. The endoscope includes one or more image sensors to capture the reflected visible light and/or the emitted fluorescence light. The fluorescence imaging system may overlay a visual representation of non-visible light onto the visible light image. However, combining or mixing the image data may result in instances where the non-visible light component is too pronounced, too light, too diffuse, or too discolored.

SUMMARY

One aspect of the disclosure provides an enhanced fluorescence imaging system including a light source configured to emit non-visible light and visible light and an image sensor including a plurality of pixels configured to capture non-visible light image data and visible light image data. The enhanced fluorescence imaging system is configured to generate a video image onto a display and includes data processing hardware in communication with the image sensor and memory hardware in communication with the data processing hardware. The memory hardware stores instructions that when executed on the data processing hardware causes the data processing hardware to perform operations that include determining, for each pixel of the plurality of pixels, a non-visible light value. The non-visible light value is associated with an amount of non-visible light captured by the image sensor. The operations also include applying a color map to each non-visible light value to associate the non-visible light value with a select color to generate non-visible light selected color values and weighting a visible light chroma value of the visible light image data with a non-visible light chroma value of the non-visible light selected color values to generate a weighted chroma value. The operations also include combining luma values of each pixel of the visible light image data to the weighted chroma values so as to enhance the video image.

Implementations of the disclosure may include one or more of the following optional features. In some implementations, the color map is configured to transform each non-visible light value to a set of values corresponding to a select color. The magnitude of the non-visible light value may be associated with an intensity of the select color. In some examples, the select color is green. Optionally, weighting the visible light chroma value of the visible light image data with the non-visible light chroma value of the non-visible light selected color values includes converting, for each pixel, the associated visible light image data into a visible light luma value, a visible light blue-difference chroma value, and a visible light red-difference chroma value and converting the non-visible light selected color values into a non-visible light luma value, a non-visible light blue-difference chroma value, and a non-visible light red-difference chroma value. Weighting the visible light chroma value of the visible light image data with the non-visible light chroma value of the non-visible light selected color may also include weighting the visible light blue-difference chroma value and the non-visible light blue-difference chroma value based on a weighting factor to generate a weighted blue-difference chroma value and weighting the visible light red-difference chroma value and the non-visible light red-difference chroma value based on the weighting factor to generate a weighted red-difference chroma value.

In some implementations, the weighting factor is based on the non-visible light value for the associated pixel. When the non-visible light value is below a first threshold value, the weighted blue-difference chroma value may be equal to the visible light blue-difference chroma value and the weighted red-difference chroma value may be equal to the visible light red-difference chroma value. When the non-visible light value is above a second threshold value, the weighted blue-difference chroma value may be equal to the non-visible light blue-difference chroma value and the weighted red-difference chroma value may be equal to the non-visible light red-difference chroma value. When the non-visible light value is between the first threshold value and the second threshold value, the weighted blue-difference chroma value may be between the visible light blue-difference chroma value and the non-visible light blue-difference chroma value and the weighted red-difference chroma value may be between the visible light red-difference chroma value and the non-visible light red-difference chroma value. Optionally, each non-visible light value is between 0 and 4095.

Another aspect of the disclosure provides a fluorescence imaging system including a light source configured to emit non-visible light and visible light and an image sensor including a plurality of pixels configured to capture non-visible light image data and visible light image data. The fluorescence imaging system is configured to generate a video image onto a display and includes data processing hardware in communication with the image sensor and memory hardware in communication with the data processing hardware. The memory hardware stores instructions that when executed on the data processing hardware cause the data processing hardware to perform operations that include determining, for each pixel of the plurality of pixels, a non-visible light value. The non-visible light value is associated with an amount of non-visible light captured by the image sensor. The operations also include adding the non-visible light value of each pixel to a select color of the visible light image data to generate added color light values. The operations also include applying a color map to each non-visible light value to associate the non-visible light value to a select color to generate a non-visible light selected color value and weighting a visible light chroma value of the visible light image data with a non-visible light chroma value of the non-visible light selected color values to generate weighted chroma values. The operations also include combining luma values of the visible light image data to the weighted chroma values to generate combined luma-chroma light values. The operations also include converting the combined luma-chroma light values into replaced color light values and weighting the added color light values with replaced color light values to generate weighted color light values so as to enhance the video image.

This aspect may include one or more of the following optional features. In some implementations, adding the non-visible light value to a select color of pixels of the visible light image data includes determining, for each pixel, a visible RGB set of values; determining, for each pixel, a non-visible light RGB set of values based on the non-visible light image data, and adding, for each pixel, the non-visible light RGB set of values to the visible RGB set of values. In some examples, weighting the added color light values with the replaced color light values include weighting based on a weighting factor. The weighting factor may be based on the non-visible light value of each associated pixel. The weighting factor, in some implementations, is based on the non-visible light value. Optionally, the weighting factor is based on the added color light values. The weighting factor may be based on a bit depth of the image sensor. In some examples, the weight of each added color light value is inversely correlated with the associated non-visible light value.

Another aspect of the disclosure provides a method for weighting image values of a fluorescence imaging system that includes a light source configured to emit non-visible light and visible light and an image sensor including a plurality of pixels configured to capture non-visible light image data and visible light image data. The fluorescence imaging system is configured to generate a video image onto a display. The method includes determining, for each pixel of the plurality of pixels, a non-visible light value. The non-visible light value is associated with an amount of non-visible light captured by the image sensor. The method also includes adding the non-visible light value of each pixel to a select color of the visible light image data to generate added color light values. The method also includes applying a color map to each non-visible light value to associate the non-visible light value to a select color to generate a non-visible light selected color value and weighting a visible light chroma value of the visible light image data with a non-visible light chroma value of the non-visible light selected color values to generate a weighted chroma value. The method also includes combining luma values of the visible light image data to the weighted chroma values to generate combined luma-chroma light values and converting the combined luma-chroma light values into replaced color light values. The method also includes weighting the added color light values with replaced color light values to generate weighted color light values The details of one or more implementations of the disclosure are set forth in the accompanying drawings and the description below. Other aspects, features, and advantages will be apparent from the description and drawings, and from the claims.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

FIG. 3 is a table of non-visible pixel values color mapped to RGB set of values.

FIG. 5 is three tables of replaced YCbCr values.

FIG. 8 is three tables of added RGB values.

DETAILED DESCRIPTION OF PREFERRED EMBODIMENTS

Figure 1:
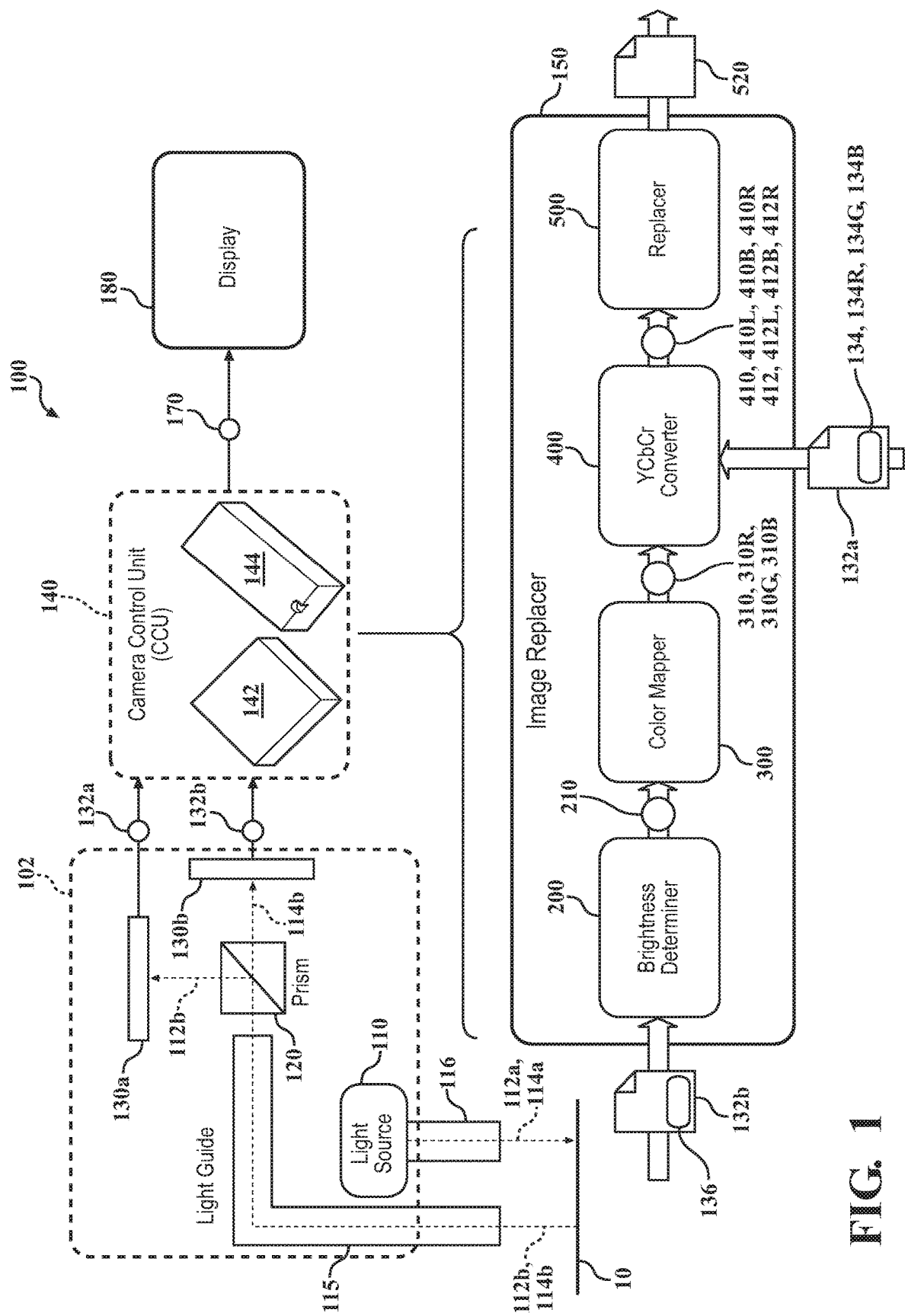
FIG. 1 is a schematic view of an example system for enhanced fluorescence imaging.

Implementations herein are directed toward an enhanced fluorescence imaging system that includes an imaging sensor that captures visible light data and non-visible light data. The system combines or blends or weights the visible light data and non-visible light data together to provide an enhanced visible light data image overlay, wherein the visible indication of the intensity of the non-visible light is not too pronounced, too light, too diffuse, or too discolored.

Many devices, such as medical tools, include imaging equipment that captures visible white light images. For example, endoscopic systems include, in their most basic form, a rigid or a flexible tube with a light source and an imaging system. The flexible tube is passed through an orifice (e.g., the mouth) of a patient and the imaging system records images illuminated by the light.

In addition to visible white light, many medical devices (such as endoscopic systems) are capable of emitting other spectrums of light (i.e., non-visible light). For example, it is common for endoscopic systems to also emit infrared light to support fluorescent imaging. The infrared light is absorbed by fluorescent dye, which in turn emits fluorescence. As used herein, the term "fluorescent dye" refers to dye approved for medical use that is configured to reflect infrared light, such as Indocyanine Green (ICG). ICG has a peak spectral absorption in the near infrared spectrum at approximately 800 nm. ICG, when irradiated with light between 750 nm and 950 nm, emits fluorescence. The endoscopic system, after irradiating the ICG with the near infrared light, detects and images this fluorescence in order to provide an image to, for example, a display that visually indicates both the visible light and the non-visible light. For example, the endoscopic system may convert the non-visible light to a select color and overlay the select color representative of the non-visible light over the visible light image.

Endoscopic systems may be equipped with one or more image sensors to image both white (i.e., visible) light and infrared light. For example, some endoscopes are equipped with a three charge-coupled device (3CCD) camera. A 3CCD camera uses a prism to split received light into three beams, one of which is directed to a red CCD, one to a green CCD, and one to a blue CCD. Endoscopic systems, in some examples, are equipped with multiple image sensors with each sensor including pixels dedicated to a respective frequency band using a color array filter commonly known as a Bayer filter (see FIG. 2). In other examples of endoscopic systems, one image sensor is equipped to simultaneously capture both visible light and infrared light. Other endoscopic systems may be equipped with multiple image sensors which individually and simultaneously capture both visible light and infrared light.

For illustrative purposes, a description of a system for optimizing blended video streams is provided within the context of an endoscopic system 100. However, it should be appreciated that the fluorescence image enhancer may be utilized in other applications, illustratively including an exoscope, borescope, videoscope and other system having two or more illumination-types and one or more image sensors. Furthermore, although the system is described with respect to medical applications using fluorescing dye, it should be understood that non-medical applications using other combinations of visible light and non-visible light may benefit from the same principles.

Referring to FIG. 1, in some implementations, an example of an endoscopic system 100 includes one or more light sources 110. The light source 110 emits both visible light (VL) 112a (e.g., white light) and non-visible light (NVL) 114a (e.g., infrared light, etc.). In some examples, the light source(s) 110 alternates between emitting VL 112a and NVL light 114a. That is, in some examples, the light source 110 rapidly switches between emitting VL 112a and NVL light 114a. In other examples, the light source(s) emit simultaneously. The VL 112a illuminates the surgical site of the system 100. The light source 110 may include one or more light-emitting diodes (LEDs) or any other appropriate light-emitting device. Separate light sources may emit the VL 112a and the NVL light 114a respectively. In some examples, the light source 110 is included within a camera head unit 102.

Light 112a, 114a emitted by the light source 110 travels along a light guide 116 (e.g., an optical fiber) and, after exiting the light guide 116, illuminates or irradiates a target area 10 (e.g., an internal cavity of a patient). Reflected VL 112b (i.e., VL 112a that has reflected from the target area 10) and, for example, emitted NVL light 114b (e.g., fluorescent light (FL)) emitted by, for example, ICG that has been irradiated by NVL light 114a, or any other form of non-visible light is directed back through an optical pathway 115 to, for example, a dichroic prism 120. The dichroic prism 120 splits received light into two beams of differing wavelengths. That is, the dichroic prism 120 splits the received light, which may include reflected VL 112b and/or NVL 114b, to image sensors 130. The image sensors 130 may include a VL image sensor 130a and an NVL image sensor 130b. For example, any reflected VL 112b (i.e., visible light) that passes through the prism 120 may be directed to the VL image sensor 130a, while any NVL 114b that passes through the prism 120 may be directed to the NVL image sensor 130b (i.e., light with a wavelength between 800 nm and 1200 nm). In some examples, the prism 120 and image sensors 130 are also included within the camera head unit 102. While a dichroic prism and two separate image sensors are illustrated, any means for capturing image data representative of both the reflected VL 112b and NVL 114b is within the spirit and scope of the appended claims.

Figure 2:
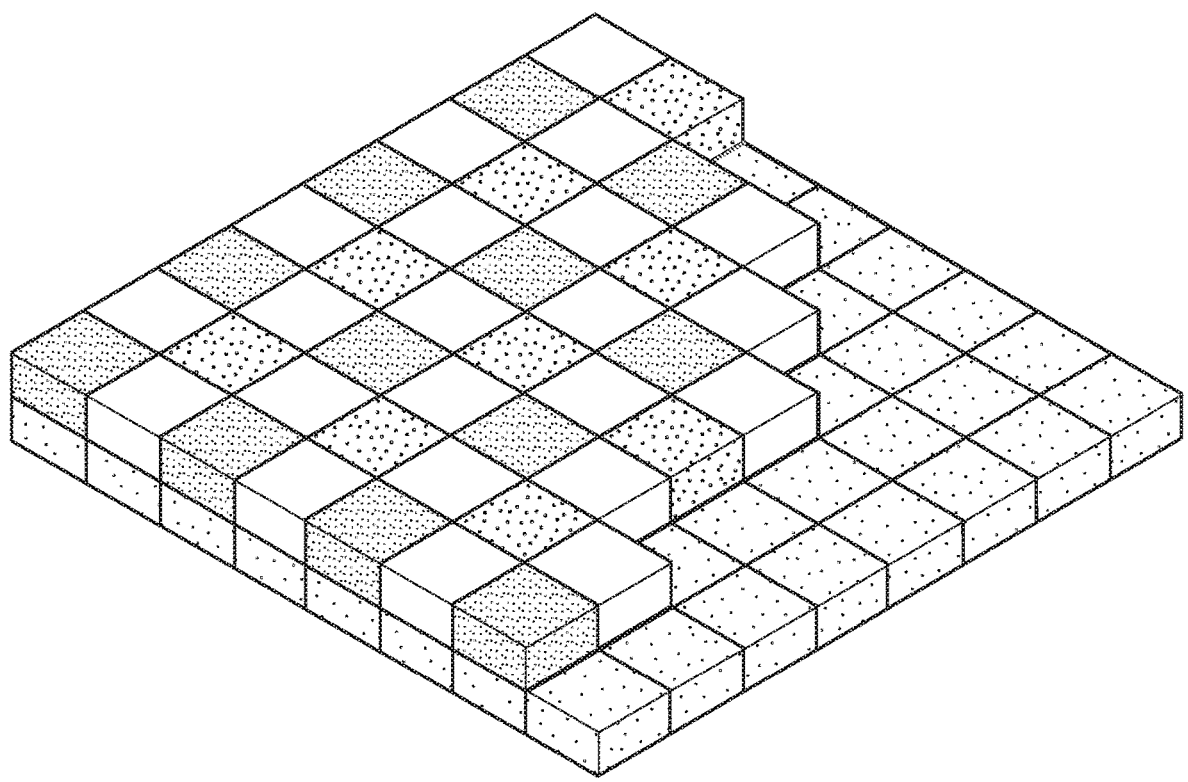
FIG. 2 is a perspective view of a known Bayer color filter array image sensor.
Figure 2:
Figure 2:
Figure 2:

The image sensors 130 may be a complementary metal oxide semiconductor (CMOS) or a Charged Coupled Device (CCD). It should be appreciated that any pixelated image sensor 130 currently known or later developed may be modified and adopted for use herein. The image sensors 130, in some implementations, include color filter arrays (CFAs). Referring now to FIG. 2, the image sensors 130 may include CFAs (sometimes referred to as a Bayer filters). Bayer CFAs include a mosaic CFA for arranging red, green, and blue color filters on a grid of photosensors. As illustrated in FIG. 2, the filter pattern is a commonly used 50% green, 25% red, and 25% blue color filter array. Thus, each pixel is filtered to record only one of the three colors, and various well-known de-mosaicking algorithms are used to obtain full-color images. In some examples, the VL image sensor 130a and the NVL image sensor 130b are different sensors with the same or different resolutions. In other examples, the image sensors 130 are identical sensors. Identical sensors (e.g., the same resolution, geometry, etc.) often improves and eases manufacturing, assembly, and alignment of the system 100. In yet other examples, a single image sensor captures both reflected VL 112b and NVL 114b.

With continued reference to FIG. 1, the sensors 130 transmit VL data 132a and NVL data 132b to a camera control unit (CCU) 140. The CCU 140 may, in some examples, be included within the camera head unit 102, while in other examples is remote from the camera head unit 102. The CCU 140 includes computing resources 142 (e.g., data processing hardware) and storage resources 144 (e.g., memory hardware). In some implementations, the CCU 140 is disposed physically at the system 100 (e.g., within the camera head unit 102) and in wired communication with the image sensors 130. In other implementations, the CCU 140 is in wireless communication with the image sensors 130 (e.g., via wireless, Bluetooth, etc.) and may be remote from the image sensors 130 and/or system 100. In this case, the CCU 140 may correspond to any appropriate computing device 1100 (see FIG. 11), such as a desktop workstation, laptop workstation, or mobile device (e.g., smart phone or tablet). In yet other implementations, the data 132 may be stored in nonvolatile storage at the system 100 (e.g., a thumb drive) and later removed to be processed at data processing and memory hardware 142, 144 remote from the image sensors 130.

VL image data 132a received by the CCU 140, in some implementations, includes data for a plurality of pixels in an RGB format. The RGB format or color model is an additive color model that represents all colors via three chromaticities of three colors: red, green, and blue. Each pixel of the VL image data 132a will have a corresponding VL RGB set of values 134 (i.e., a VL RGB red value 134R, a VL RGB green value 134G, and a VL RGB blue value 134B). Each VL RGB set of values 134 includes a numerical value between a minimum VL RGB value and a maximum VL RGB value. The minimum and maximum values may be dependent upon the image sensor 130. More specifically, the values may be dependent upon a color bit depth of the image sensor 130. For example, when the image sensor 130 has a 12-bit bit depth, the minimum value may be 0 while the maximum value may be 4095. The VL RGB values 134 may be based upon processing pixel information from the image sensor 130, such as with a color filter array (e.g., a Bayer filter) (FIG. 2).

The data processing hardware 142, in some implementations, executes (i.e., using instructions stored on the storage resources 144) an image replacer 150. The image replacer 150 receives the NVL data 132b at an intensity pixel value determiner 200. In some examples, the intensity value determiner 200 determines a non-visible light value 210 (or NVL value) for each pixel 136 of the NVL image data 132b. For example, image data captured by the image sensor 130b of non-visible light may be represented as a grayscale image with each value of each pixel of the image ranging from a minimum NVL value to a maximum NVL value. That is, in some examples, the more NVL the pixel detects or captures, the greater (up to the maximum NVL value) the NVL value 210 will be. For example, a pixel 136 with a minimum NVL value 210 (e.g., zero) may be represented as black on the grayscale image while a pixel 136 with a maximum NVL value 210 (e.g., 4095 for 12-bit depth) may be represented as white on the grayscale image.

The NVL values 210, in some implementations, are passed to a color mapper 300. The color mapper 300 maps or assigns or converts the NVL values 210 to a select color map in the RGB format to generate non-visible light RGB selected color sets of values 310. Each NVL RGB selected color set of values 310 includes an NVL RGB red value 310R, an NVL RGB green value 310G, and an NVL blue value 210B. While in the examples provided the select color is green only, any other color map may also be selected, including blue only, red only, blended single color such as orange, yellow, purple, etc., or a multicolor often referred to colloquially as a "heat map" look-up table (LUT).

Referring now to FIG. 3, three exemplary NVL values 210 (NVL) and resulting non-visible light RGB selected color sets of values 310 after color mapping are illustrated. Here, 'R' represents the NVL RGB red value 310R, 'G' represents the NVL RGB green value 310G, and 'B' represents the NVL RGB blue value 310B. In this example, the color mapper 300 maps each NVL value 210 to green. For example, when NVL is equal to 50, R is equal to 0, G is equal to 50, and B is equal to 0. When NVL is equal to 150, R is equal to 0, G is equal to 150, and B is equal to 0. Similarly, when NVL is equal to 250, R is equal to 0, G is equal to 250, and B is equal to 0. That is, in some implementations, the color mapper 300 takes RGB values of all zeroes and adds the NVL value 210 to the selected color (green in the illustrated example).

YCbCr is a color space that separates color into a luma component (Y), a blue-difference component (Cb) and a red-difference component (Cr). In some implementations, a YCbCr converter 400 (as depicted in FIG. 1) receives the VL RGB values 134 and the NVL RGB selected color sets of values 310, each of which are in RGB format, and converts each value to VL YCbCr values 410 and NVL YCbCr values 412 respectively. Each of the VL YCbCr values 410 comprise a VL luma (Y) value 410L, a VL blue-difference chroma (Cb) value 410B, and a VL red-difference chroma (Cr) value 410R. Similarly, the NVL YCbCr values 412 each include an NVL luma value 412L, an NVL blue-difference chroma value 412B, and an NVL red-difference chroma value 412R. The conversion from RGB color space to YCbCr color space may be accomplished through commonly known means.

In some examples, a replacer 500 (shown in FIG. 1) receives the VL YCbCr values 410 and the NVL YCbCr values 412 from the YCbCr converter 400. The replacer 500 may combine or blend or weight the VL blue-difference chroma value 410B with the NVL blue-difference chroma value 412B and the VL red-difference chroma value 410R with the NVL red-difference chroma value 412R. The blending or combining may be based on a weighting factor 510. Optionally, the weighting factor varies per pixel based on the NVL value 210 (i.e., each pixel is weighted differently depending on the associated NVL value 210).

Figure 4:
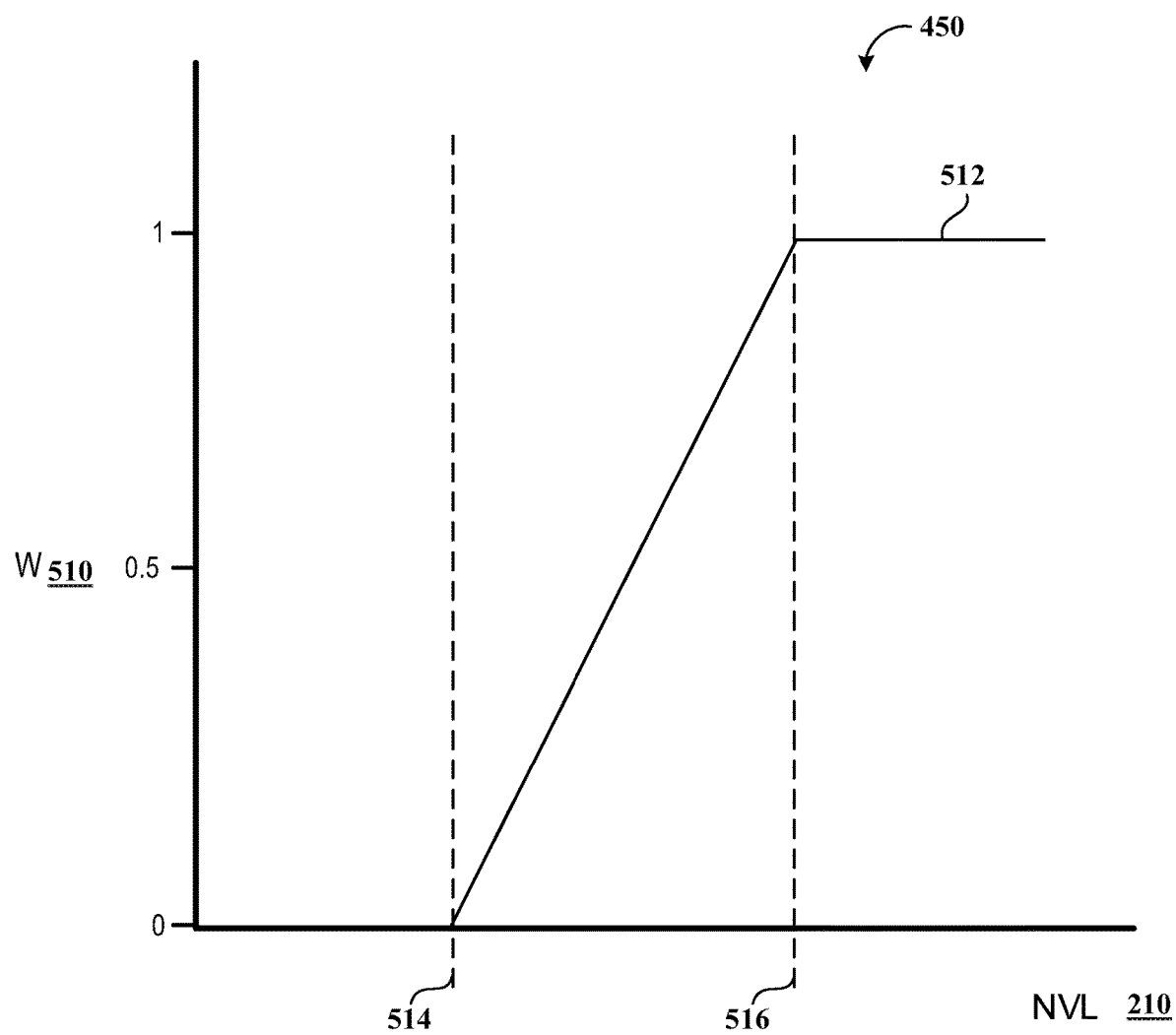
FIG. 4 is a graph of a weighting function for selected YCbCr values.

Referring now to FIG. 4, an exemplary graph 450 of a replace weighting function 512 is illustrated. Here, when the NVL value 210 is below a first replace threshold 514, the weighting factor 510 is zero and when the NVL value 210 is above a second replace threshold 516, the weighting factor is one. When the NVL value 210 is above the first replace threshold 514 and below the second replace threshold 516 (i.e., the NVL value 210 is between the two thresholds 514, 516), the weighting factor 510 may scale linearly with the NVL value 210. Alternatively, the weighting factor 510 may scale exponentially, logarithmically, etc. The first replace threshold 514 and the second replace threshold 516 may be adjusted to be between a minimum NVL value and a maximum NVL value to produce various desired results in the final enhanced image frame 170. In some examples, the replacer 500 weights the VL CbCr values 410B, 410R and the NVL CbCr values 412B, 412R with Equation 1 (produced below) to generate a weighted blue-difference chroma value 520B ($Cb_w$) and a weighted red-difference chroma value 520R ($Cr_w$), where w is the weighting factor.

$$(w)(Cb_{NVL}Cr_{NVL})+(1-w)(Cb_{VL}Cr_{VL})=Cb_wCr_w \quad (1)$$

Thus, in some examples, when the NVL value 210 is below the first replace threshold 514, the weighting factor 510 is zero and $Cb_wCr_w$ is equal to $Cb_{VL}Cr_{VL}$ (i.e., the NVL image data is not used because the weighting factor zeros out the $Cb_{NVL}Cr_{NVL}$ contribution). When the NVL value 210 is above the second replace threshold 516, the weighting factor 510 is one and $Cb_wCr_w$ is equal to $Cb_{NVL}Cr_{NVL}$ (i.e., $Cb_{VL}Cr_{VL}$ is entirely replaced by $Cb_{NVL}Cr_{NVL}$ because the weighting factor zeros out the $Cb_{VL}Cr_{VL}$ contribution). In between the first replace threshold 514 and the second replace threshold 516, weighting factor 510 increases the weight or contribution of the NVL CbCr values 412B, 412R to the $Cb_wCr_w$ values (while reducing the weight or contribution of the VL CbCr values 410B, 410R) as the NVL value 210 increases.

The replacer 500, in some implementations, combines the VL luma value 410L with the weighted blue-difference chroma value 520B and the red-difference chroma value 520R to generate replaced color light values 520 (i.e., replaced YCbCr values or $Y_{VL}Cb_wCr_w$). That is, the replacer 500 may replace the CbCr chroma values of the VL YCbCr values 410 with the weighted CbCr values 520B, 520R while maintaining the original VL luma values 410L.

Referring now to FIG. 5, tables 560a-c provide examples of the replacer 500 replacing the CbCr values. Table 560a assumes the NVL value 210 is 50 while the VL RGB red value 134R is 200, the VL RGB green value 134G is 150, and the VL RGB blue value 134B is 150. In this example, the depth is eight bits, and therefore the maximum value for each value is 255. Also in this example, the first replace threshold 514 is 100 and the second replace threshold is 200. Still referring to table 560a, after converting the VL RGB values 134 to YCbCr (i.e., at the YCbCr converter 400), the VL luma value 410L is 158, the VL blue-difference chroma value 410B is 121, and the VL red-difference chroma value 410R is 150. After converting the NVL RGB selected color values 310 to YCbCr, the NVL luma value 412L is 41, the NVL blue-difference chroma value 412B is 113, and the NVL red-difference chroma value 412R is 110. That is, because the NVL value (i.e., 50) is below the first replace threshold 514 (i.e., 100), the weighted CbCr values 520B, 520R are equal to the VL CbCr values 410B, 410R. The replacer 500, regardless of the NVL value 210, combines the NVL luma value 412L with the weighted CbCr values 520B, 520R to generate the final YCbCr value 520.

Table 560b assumes the NVL value 210 is 150, which is above the first replace threshold 514 (100 in this example) and below the second replace threshold 516 (200 in this example). After conversion to YCbCr, the NVL YCbCr values include the NVL luma value 412L of 92, the NVL blue-difference chroma value 412B of 84, and the NVL red-difference chroma value 412R of 73. Using the same VL YCbCr values 410 (i.e., Y=158, Cb=121, and Cr=150), the weighted blue-difference chroma value 520B is 103 and the weighted red-difference chroma value 520R is 112. In this case, because the NVL value 210 is between the first replace threshold 514 and the second replace threshold 516, the weighted CbCr values 520B, 520R are a combination of the NVL and VL values based on the weighting factor 510. Again, the replacer 500, regardless of the NVL value 210, combines the NVL luma value 412L with the weighted CbCr values 520B, 520R to generate the final YCbCr value 520.

Table 560c assumes the NVL value 210 is 250, which is above the first and the second replace thresholds 514, 516 (100 and 200 respectively in this example). After conversion to YCbCr, the NVL YCbCr values include the NVL luma value 412L of 142, the NVL blue-difference chroma value 412B of 55, and the NVL red-difference chroma value 412R of 36. Using the same VL YCbCr values 410 (i.e., Y=158, Cb=121, and Cr=150), the weighted blue-difference chroma value 520B is 55 and the weighted red-difference chroma value 520R is 36. That is, because the NVL value 210 exceeded the second replace threshold, the weighted CbCr 520B, 520R values are equal to the NVL CbCr values 412B, 412R (i.e., the VL CbCr values are completely replaced). Again, the replacer 500, regardless of the NVL value 210, combines the NVL luma value 412L with the weighted CbCr values 520B, 520R to generate the final YCbCr value 520.

Thus, as illustrated in the tables of FIG. 5, in some implementations, when the NVL value 210 is below the first replace threshold 514, the final YCbCr value 520 completely eliminates the NVL CbCr values 412B, 412R (i.e., the final CbCr values 520 are equal the VL CbCr values 410). When the NVL value 210 is above the second replace threshold 516, which is greater that the first replace threshold 514, the VL CbCr values 410B, 410R are completely replaced by the NVL CbCr values 412B, 412R (i.e., the final CbCr values 520 are equal to the NVL CbCr values 412). For NVL values 210 between the first replace threshold 514 and the second replace threshold 516, the replacer 500 may combine or blend or weight the VL CbCr values 410B, 410R and the NVL CbCr values 412B, 412R together. Regardless of the NVL value 210, the VL luma value 410L is combined with the weighted CbCr values 520B, 520R. The image replacer 150 processes each pixel of VL image data 132a and NVL image data 132b to generate an enhanced image frame 170 that includes the VL luma value 410L and the weighted CbCr values 520B, 520R for each pixel of the image for displaying on the display 180. In some examples, the final YCbCr value 520 may be converted to the RGB format and/or undergo additional filtering or processing prior to transmission to the display.

Figure 6:
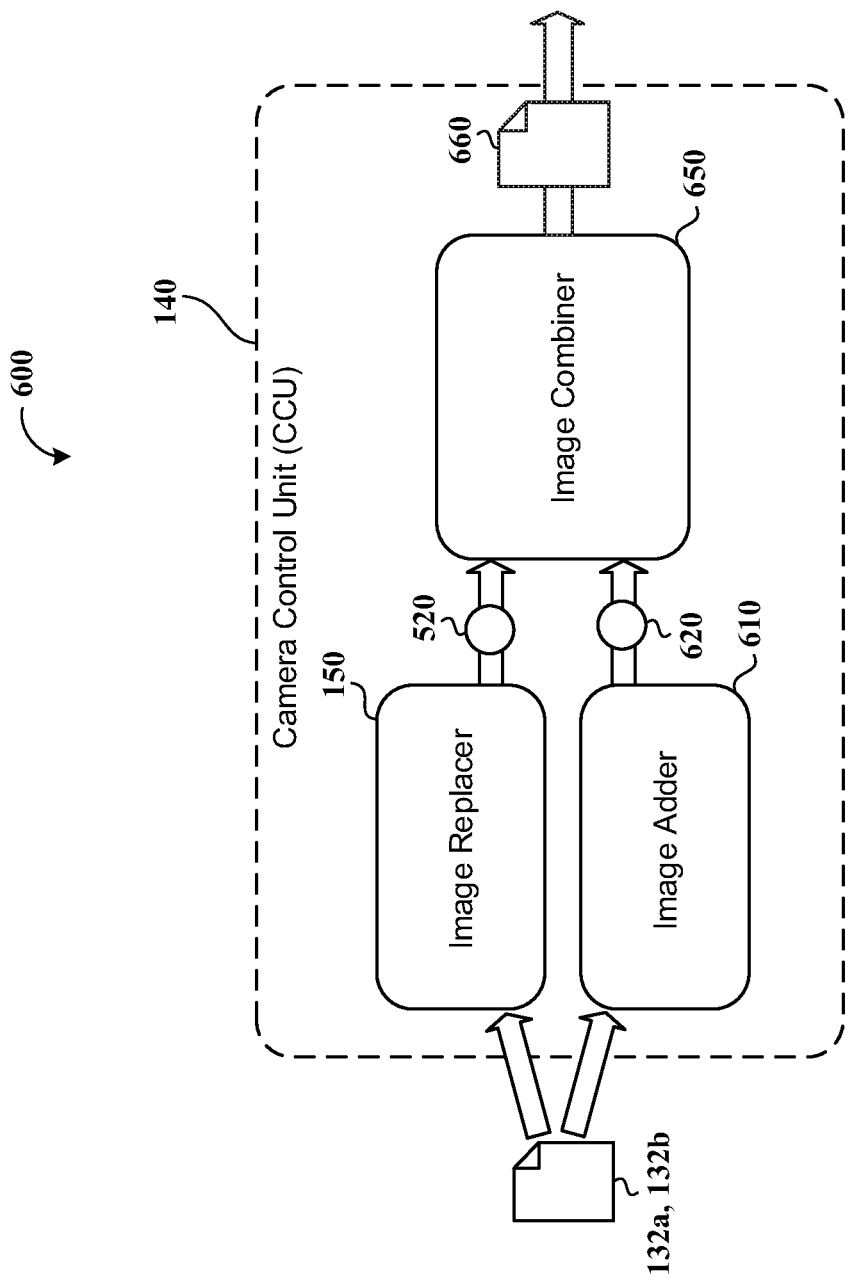
FIG. 6 is a schematic view of another example system for enhanced fluorescence imaging.
Figure 7:
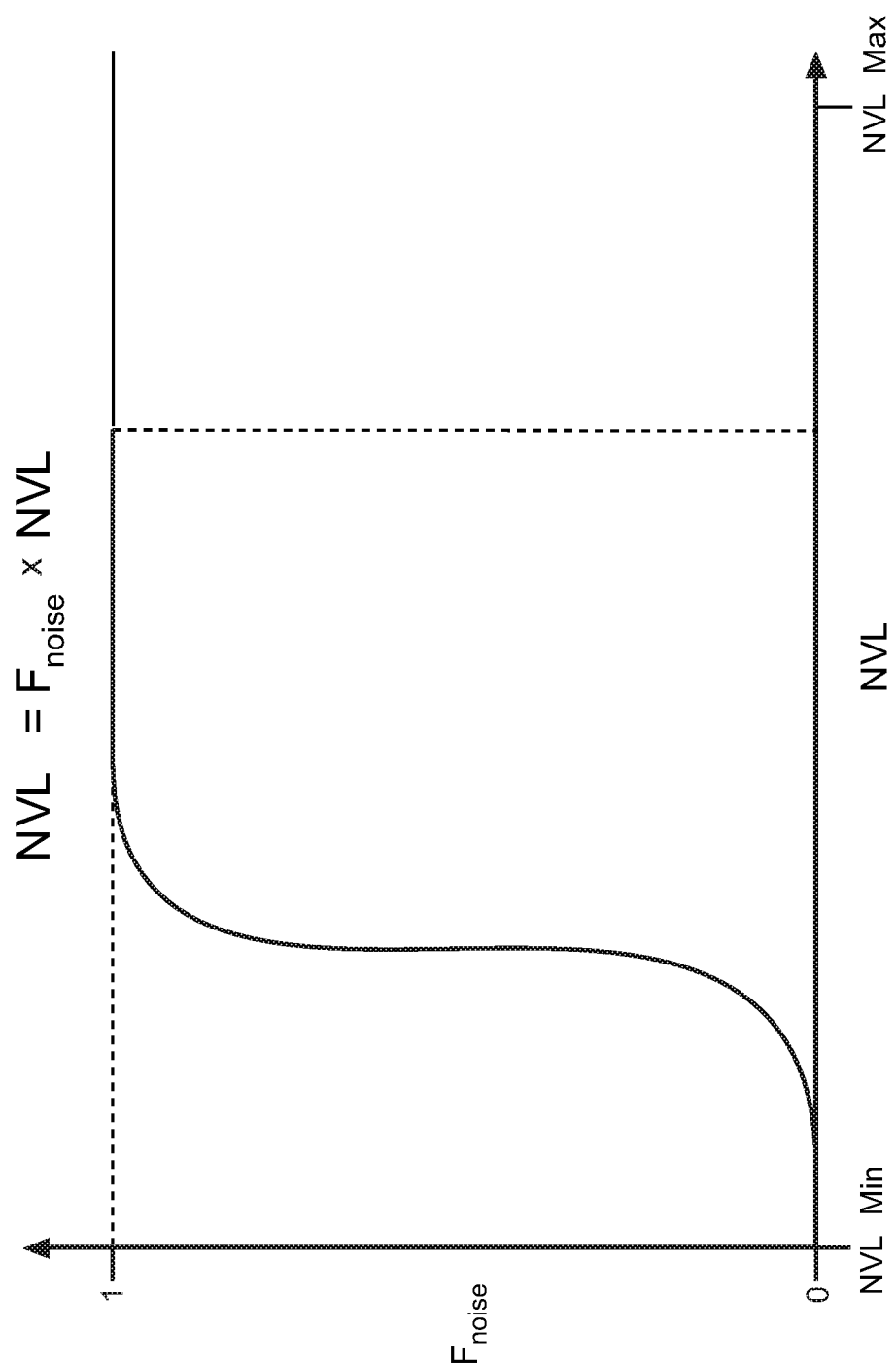
FIG. 7 is a graph of a look-up table.

In some implementations, the CCU 140 executes the image replacer 150 and an image adder 610 simultaneously. Referring now to FIG. 6, both the image replacer 150 and the image adder 610 receive the VL image data 132a and the NVL image data 132b and obtain the NVL value 210 of each pixel 136. The image adder 610 may add the NVL value 210 of each pixel to a select color (e.g., green) of the corresponding VL RGB value 134. For example, when the select color is green, each NVL value 210 may be added directly to the VL RGB green value 134G to generate added color light values 620 (herein also referred to as added RGB values). In some implementations, the added RGB values 620 are further processed or weighted. For example, FIG. 7 illustrates an exemplary graph of a weighting function or multiplier to, for example, remove low level noise. In this example, the x-axis represents the NVL value 210 (from 0 up to the maximum allowed value). The y-axis represents a multiplier or weight factor that ranges from 0 to 1. The value of the multiplier is multiplied by the NVL value 210 to generate modified NVL values 210 or added RGB values 620. In this case, above a threshold value, the multiplier is one and the full NVL value 210 is used, while below a threshold value, the multiplier is zero and the NVL value 210 is also zero.

Referring now to FIG. 8, three exemplary tables 860a, 860b, and 860a illustrate the added RGB values 620 in three examples that mirror the examples from FIG. 5. Here, the bit depth is again eight bits, so each RGB value has a maximum of 255. Table 860a illustrates an NVL value of 50. As with tables 560a-c, the VL RGB value 134 is 200 for red, 150 for green, and 150 for blue. After the image adder 610 adds the NVL value 210 to the select color (green in this example), the added RGB values 620 include 200 for red (the same as the VL RGB red value 134R), 200 for green (the VL RGB green value 134G of 150 summed with the NVL value 210 of 50), and 150 for blue (the same as the VL RGB blue value 134B).

Table 860b illustrates the same VL RGB values 134 with an NVL value 210 of 150. As with table 860a, the added RGB value 620 includes a red value of 200 and a blue value of 150. Here, the added RGB green value is 255, as the VL RGB green value of 150 summed with the NVL value 210 of 150 equals 300, which exceeds the maximum value of 255. Thus, in this case, the addition of the NVL value 210 to the VL RGB green value 134G causes the value to clip. That is, the actual value is lost due to exceeding the maximum value allowed by the bit depth. Table 860c illustrates the same VL RGB values 134 with an NVL value 210 of 250. As with the previous tables 860a, 860b, the added RGB value 620 includes a red value of 200 and a blue value of 150. In this case, the added RGB green value is again 255, as the VL RGB green value of 150 summed with the NVL value 210 of 250 equals 400, which exceeds the maximum value of 255. Thus, despite the NVL value 210 of table 860c being greater than the NVL value 210 of table 860b, due to clipping both values are the same in the added RGB values 620 and the difference in NVL is lost.

To alleviate clipping, the image replacer 150 may be executed simultaneously with the imager adder 610. Referring back to FIG. 6, an image combiner 650 may receive the final YCbCr values 520 from the image replacer 150 and the added RGB values 620 from the image adder. The image combiner 650, in some examples, converts the final YCbCr values 520 from the image replacer to RGB format to generate replaced RGB values 630. Alternatively, the imager replacer 150 may generate the replaced RGB values 630 prior to transmission to the image combiner 650.

Figure 9:
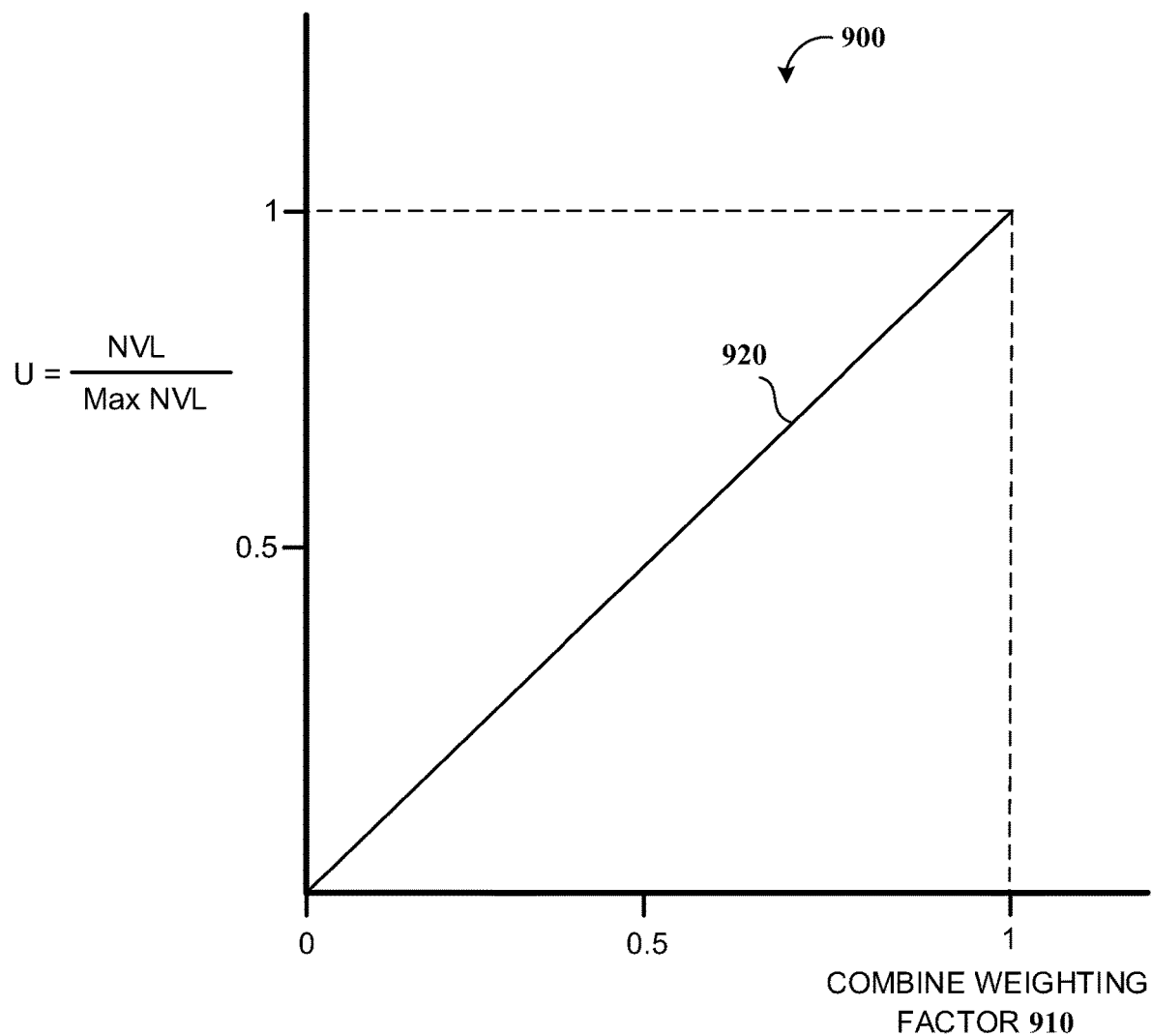
FIG. 9 is a plot of a combine weighting function.

In some implementations, the image combiner 650 combines or blends or weights the added RGB values 620 with the replaced RGB values 630 based on a combine weighting factor 910 (FIG. 9). In some examples, the image combiner 650 weights the added RGB values 620 with the replaced RGB values 630 with the weighting factor 910 using Equation 2 (provided below) to generate final RGB values 660, where u represents the weighting factor 910, $RGB_{add}$ represents the added RGB values 620, and $RGB_{rep}$ represents the replaced RGB values 630.

$$(1-u)(RGB_{add})+(u)(RGB_{rep})=RGB_{final} \qquad (2)$$

Referring now to FIG. 9, an exemplary graph 900 of a combine weighting function 920 is illustrated. Here, the x-axis is the combine weighting factor 910 which may be a value between 0 and 1. The y-axis of graph 900 is the NVL value 210 divided by the maximum allowed NVL value. The maximum value may be based on the color bit depth of the image sensor. For example, an 8-bit depth would have a maximum value of 255 while a 12-bit depth would have a maximum value of 4095. As the NVL value 210 increases (i.e., the ratio between the NVL value 210 and the maximum value approaches one), the combine weighting factor 910 increases. In some implementations, when the NVL value 210 is equal to the maximum value, the combine weighting factor 910 is equal to one and when the NVL value 210 is equal to zero, the combine weighting factor 910 is also equal to zero.

Thus, using the combine weighting factor 910, the image combiner 650 combines or blends the added RGB values 620 with the replaced RGB values 630. As the added RGB values 620 approach the maximum value 914 (i.e., the added RGB value approaches clipping), the replaced RGB values have increased weight such that when the added RGB value 620 is equal to the maximum value 914, the final RGB value 660 is equal to the replaced RGB value 630. Similarly, as the added RGB value 620 decreases (i.e., approaches zero), the added RGB values 620 have increased weight such that when the added RGB value 620 is equal to zero, the final RGB value 660 is equal to the added RGB value 620.

The CCU 140, after processing and enhancing the image data 132*a*, 132*b*, outputs the enhanced image frame 170 to the display 180. The enhanced image frame 170 includes imagery based on the NVL image data 132*b* and the VL image data 132*a*. In some examples, the image frame 170 may undergo further processing prior to transmission to the display (e.g., filtering, etc.). The display processes the image frame 170 to generate a visible image (i.e., a picture or video).

Accordingly, the endoscopic system 100 provided may combine or blend visible light image data and non-visible light image data (e.g., infrared image data) to generate an enhanced image frame that maps the non-visible light to a select color. The system 100 ensures that the visible indication of the non-visible light image data (i.e., the select color overlay) is not too pronounced, too light, too diffuse, or too discolored after combining or blending the image data by using a variable weighting factor based on the intensity of the non-visible light.

Figure 10:
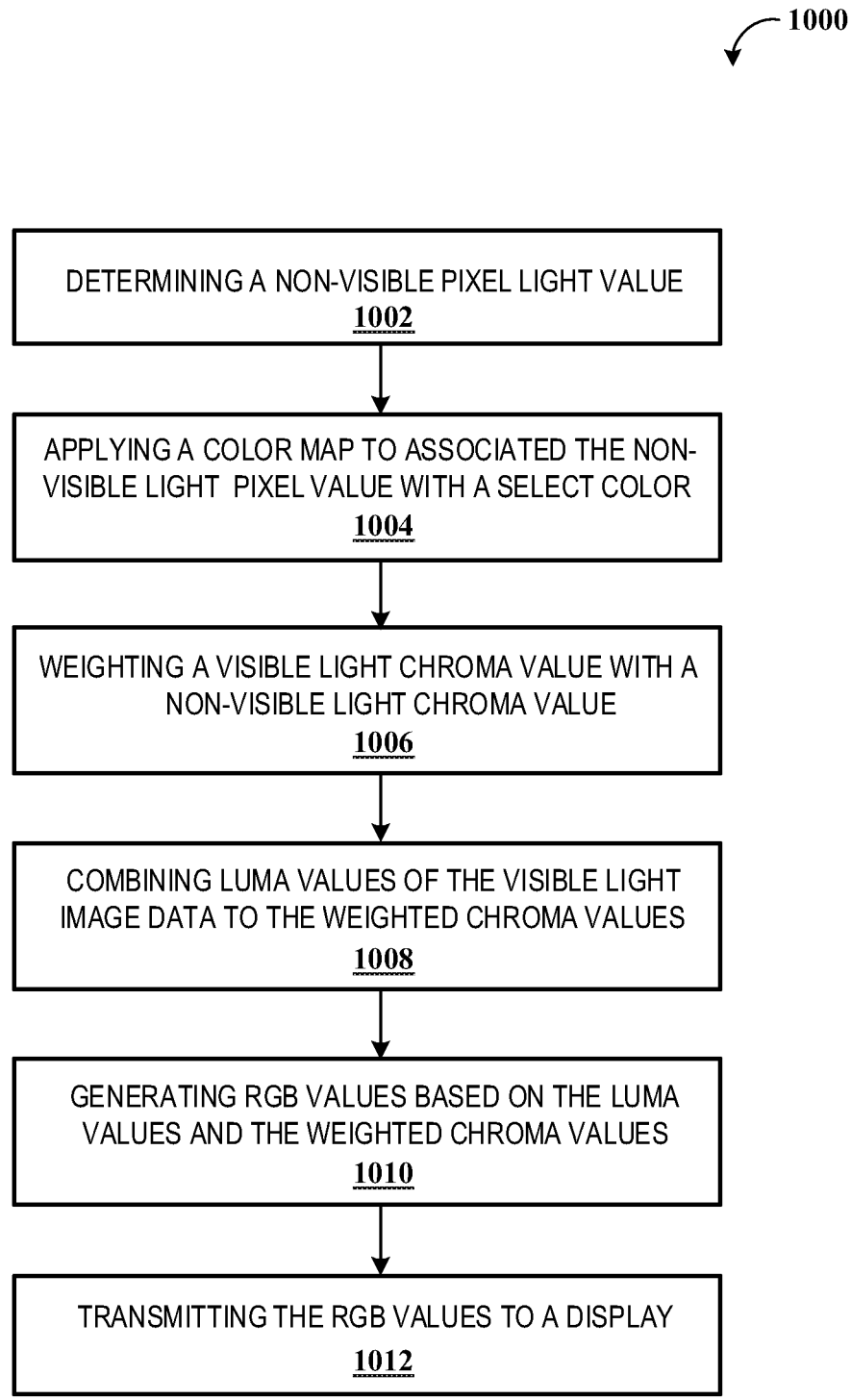
FIG. 10 is a flowchart of an example method enhancing fluorescence imaging.

FIG. 10 is a flowchart of example operations 1000 for an enhanced fluorescence imaging system 100 that is configured to emit non-visible light and visible light and an image sensor including a plurality of pixels configured to capture non-visible light image data and visible light image data. The imaging system is configured to generate a video image onto a display. The system and also includes data processing hardware in communication with the image sensor and memory hardware in communication with the data processing hardware. The memory hardware stores instructions that when executed on the data processing hardware cause the data processing hardware to perform operations. The operations include, at step 1002, determining, for each pixel of the plurality of pixels, a non-visible value. The non-visible value is associated with an amount of non-visible light captured by the image sensor.

The operations, at step 1004, also include applying a color map to each non-visible value to associate the non-visible value to a select color to generate non-visible light selected color values. At step 1006, the operations include weighting a visible light chroma value of the visible light image data with a non-visible light chroma value of the non-visible light selected color values to generate weighted chroma values. At step 1008, the operations include combining luma values of each pixel of the visible light image data to the weighted chroma values. The operations also include, at step 1010, generating RGB values based on the luma values of the visible light image data and the weighted chroma values, and at operations at step 1012, transmitting the RGB values to the display.

Figure 11:
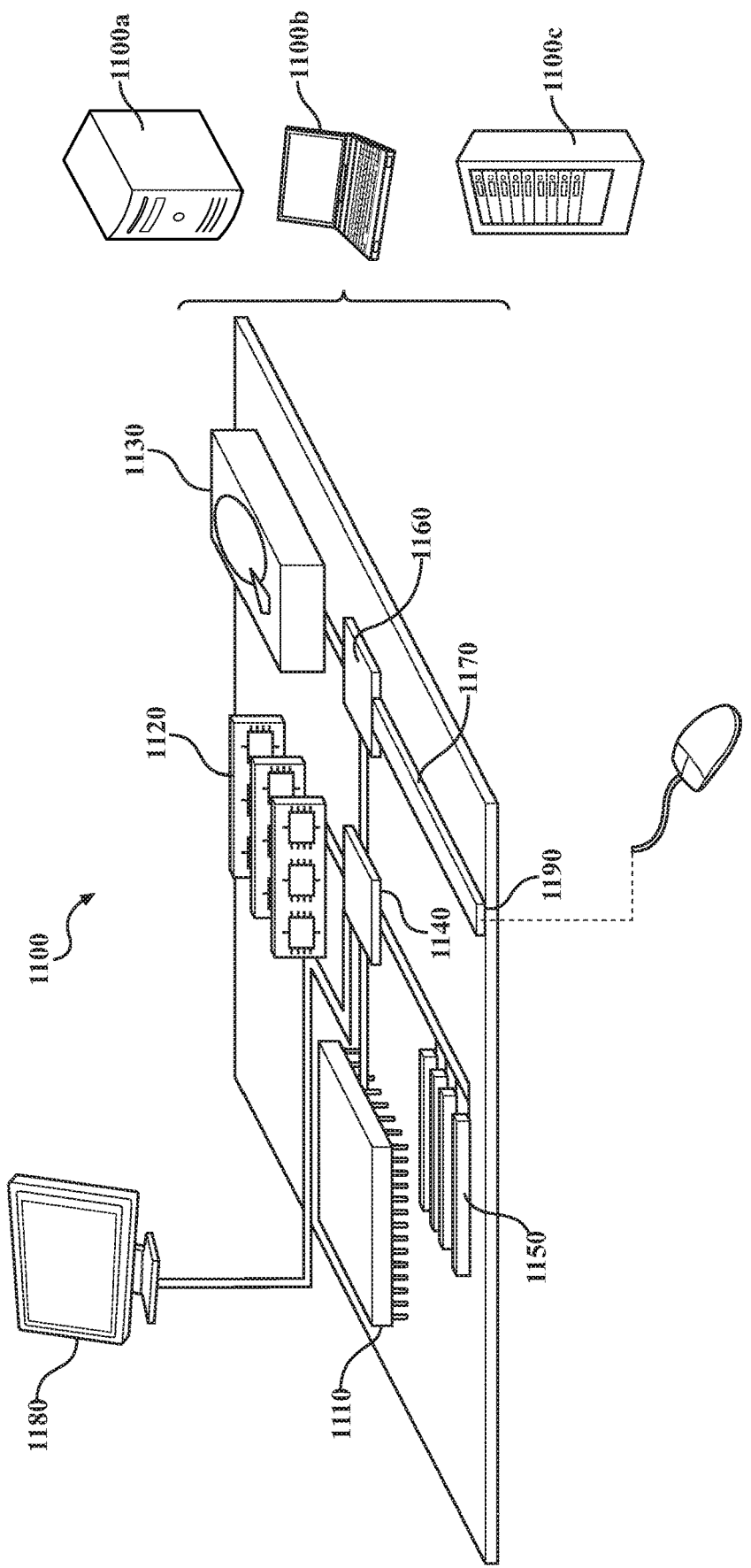
FIG. 11 is a schematic view of an example computing device that may be used to implement the systems and methods described herein.

FIG. 11 is schematic view of an example computing device 1100 (e.g., data processing hardware 142 and memory hardware 144) that may be used to implement the systems and methods described in this document. For examples, computing device 1100 may perform tasks such as controlling the light source 110 (e.g., enabling and disabling the light source, switching between white light and near-infrared (NIR) light, etc.), configuring and communicating with the image sensors 130 (e.g., receiving the image data), and implementing and executing one or more components 200, 300, 400, 500 of the system 100. In some examples, the computing device 1100 transmits image data to the display 180. That is, using the data received from the image sensors 130, the computing device 1100 may store and execute instructions or operations to implement components 200, 300, 400, 500, etc. The computing device 1100 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the disclosures described and/or claimed in this document.

The computing device 1100 (e.g., data processing hardware 142) includes a processor 1110, memory 1120, a storage device 1130, a high-speed interface/controller 1140 connecting to the memory 1120 and high-speed expansion ports 1150, and a low speed interface/controller 1160 connecting to a low speed bus 1170 and a storage device 1130. Each of the components 1110, 1120, 1130, 1140, 1150, and 1160, are interconnected using various busses, and may be mounted on a common motherboard or in other manners as appropriate. The processor 1110 can process instructions for execution within the computing device 1100, including instructions stored in the memory 1120 or on the storage device 1130 to display graphical information for a graphical user interface (GUI) on an external input/output device, such as display 1180 coupled to high speed interface 1140. In other implementations, multiple processors and/or multiple buses may be used, as appropriate, along with multiple memories and types of memory. Also, multiple computing devices 1100 may be connected, with each device providing portions of the necessary operations (e.g., as a server bank, a group of blade servers, or a multi-processor system).

The memory 1120 stores information non-transitorily within the computing device 1100. The memory 1120 may be a computer-readable medium, a volatile memory unit(s), or non-volatile memory unit(s). The non-transitory memory 1120 may be physical devices used to store programs (e.g., sequences of instructions) or data (e.g., program state information) on a temporary or permanent basis for use by the computing device 1100. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 1130 is capable of providing mass storage for the computing device 1100. In some implementations, the storage device 1130 is a computer-readable medium. In various different implementations, the storage device 1130 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 1120, the storage device 1130, or memory on processor 1110.

The high speed controller 1140 manages bandwidth-intensive operations for the computing device 1100, while the low speed controller 1160 manages lower bandwidth-intensive operations. Such allocation of duties is exemplary only. In some implementations, the high-speed controller 1140 is coupled to the memory 1120, the display 1180 (e.g., through a graphics processor or accelerator), and to the high-speed expansion ports 1150, which may accept various expansion cards (not shown). In some implementations, the low-speed controller 1160 is coupled to the storage device 1130 and a low-speed expansion port 1190. The low-speed expansion port 1190, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1100a or multiple times in a group of such servers 1100a, as a laptop computer 1100b, or as part of a rack server system 1100c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A fluorescence imaging system comprising a light source configured to emit non-visible light and visible light and an image sensor including a plurality of pixels configured to capture non-visible light image data and visible light image data, the fluorescence imaging system configured to generate a video image onto a display, the fluorescence imaging system comprising:

data processing hardware in communication with the image sensor; and memory hardware in communication with the data processing hardware, the memory hardware storing instructions that when executed on the data processing hardware cause the data processing hardware to perform operations comprising:

determining, for each pixel of the plurality of pixels, a non-visible light value, the non-visible light value associated with an amount of non-visible light captured by the image sensor;

applying a color map to each non-visible light value to associate the non-visible light value with a select color to generate non-visible light selected color values;

converting, for each pixel, the associated visible light image data into a visible light luma value, a visible light blue-difference chroma value, and a visible light red-difference chroma value;

converting the non-visible light selected color values into a non-visible light luma value, a non-visible light blue-difference chroma value, and a non-visible light red-difference chroma value;

weighting the visible light blue-difference chroma value and the non-visible light blue-difference chroma value based on a weighting factor to generate a weighted blue-difference chroma value;

weighting the visible light red-difference chroma value and the non-visible light red-difference chroma value based on the weighting factor to generate a weighted red-difference chroma value; and combining luma values of each pixel of the visible light image data to the weighted blue-difference and red-difference chroma values so as to enhance the video image.

2. The fluorescence imaging system of claim 1, wherein the color map is configured to transform each non-visible light value to a select color, the magnitude of the non-visible light value associated with an intensity of the select color.

3. The fluorescence imaging system of claim 1, wherein the select color is green.

4. The fluorescence imaging system of claim 1, wherein the weighting factor is based on the non-visible light value for the associated pixel.

5. The fluorescence imaging system of claim 4, wherein when the non-visible light value is below a first threshold value, the weighted blue-difference chroma value is equal to the visible light blue-difference chroma value and the weighted red-difference chroma value is equal to the visible light red-difference chroma value.

6. The fluorescence imaging system of claim 5, wherein when the non-visible light value is above a second threshold value, the weighted blue-difference chroma value is equal to the non-visible light blue-difference chroma value and the weighted red-difference chroma value is equal to the non-visible light red-difference chroma value.

7. The fluorescence imaging system of claim 6, wherein when the non-visible light value is between the first threshold value and the second threshold value, the weighted blue-difference chroma value is between the visible light blue-difference chroma value and the non-visible light blue-difference chroma value and the weighted red-difference chroma value is in between the visible light red-difference chroma value and the non-visible light red-difference chroma value.

8. The fluorescence imaging system of claim 1, wherein each non-visible light value is between a non-visible light minimum value and a non-visible light maximum value based on a pixel bit depth.

9. A fluorescence imaging system including a light source configured to emit non-visible light and visible light and an image sensor comprising a plurality of pixels configured to capture non-visible light image data and visible light image data, the fluorescence imaging system configured to generate a video image onto a display, the fluorescence imaging system comprising:

data processing hardware in communication with the image sensor; and memory hardware in communication with the data processing hardware, the memory hardware storing instructions that when executed on the data processing hardware cause the data processing hardware to perform operations comprising:

determining, for each pixel of the plurality of pixels, a non-visible light value, the non-visible light value associated with an amount of non-visible light captured by the image sensor;

adding the non-visible light value of each pixel to a select color of the visible light image data to generate added color light values;

applying a color map to each non-visible light value to associate the non-visible light value with a select color to generate a non-visible light selected color value;

weighting a visible light chroma value of the visible light image data with a non-visible light chroma value of the non-visible light selected color values to generate weighted chroma values;

combining luma values of the visible light image data to the weighted chroma values to generate combined luma-chroma light values;

converting the combined luma-chroma light values into replaced color light values; and weighting the added color light values with replaced color light values to generate weighted color light values so as to enhance the video image.

10. The fluorescence imaging system of claim 9, wherein adding the non-visible light value to a select color of pixels of the visible light image data includes:

determining, for each pixel, a visible RGB value;

determining, for each pixel, a non-visible light RGB value based on the non-visible light image data; and adding, for each pixel, the non-visible light RGB value the visible RGB value.

11. The fluorescence imaging system of claim 10, wherein weighting the added color light values with the replaced color light values comprises weighting based on a weighting factor, the weighting factor based on the non-visible light value of each associated pixel.

12. The fluorescence imaging system of claim 11, wherein the weighting factor is based on the non-visible light value.

13. The fluorescence imaging system of claim 11, wherein the weighting factor is based on the added color light values.

14. The fluorescence imaging system of claim 11, wherein the weighting factor is based on a bit depth of the image sensor.

15. The fluorescence imaging system of claim 10, wherein the weight of each added color light value is inversely correlated with the associated non-visible light value.

16. A method for weighting image values of a fluorescence imaging system comprising a light source configured to emit non-visible light and visible light and an image sensor comprising a plurality of pixels configured to capture non-visible light image data and visible light image data, the fluorescence imaging system configured to generate a video image onto a display, the method comprising:

determining, for each pixel of the plurality of pixels, a non-visible light value, the non-visible light value associated with an amount of non-visible light captured by the image sensor;

adding the non-visible light value of each pixel to a select color of the visible light image data to generate added color light values;

applying a color map to each non-visible light value to associate the non-visible light value with a select color to generate a non-visible light selected color value;

weighting a visible light chroma value of the visible light image data with a non-visible light chroma value of the non-visible light selected color values to generate a weighted chroma value;

combining luma values of the visible light image data to the weighted chroma values to generate combined luma-chroma light values;

converting the combined luma-chroma light values into replaced color light values; and weighting the added color light values with replaced color light values to generate weighted color light values.

\* \* \* \* \*